United States Patent [19]

Salem et al.

[11] Patent Number: 4,921,789

[45] Date of Patent: May 1, 1990

[54] MARKER FOR COLORECTAL CARCINOMA AND METHODS OF DETECTING THE SAME

[75] Inventors: Ronald R. Salem, Brookline; Peter Thomas, Pembroke; Glenn Steele, Swampscott, all of Mass.

[73] Assignee: New England Deaconess Hospital Corporation, Boston, Mass.

[21] Appl. No.: 184,079

[22] Filed: Apr. 20, 1988

[51] Int. Cl.$^5$ ............... G01N 33/53; G01N 33/566; G01N 33/563; C12M 15/00

[52] U.S. Cl. .................... 435/7; 435/172.2; 435/240.26; 435/240.27; 435/810; 436/501; 436/512; 436/548; 436/808; 436/813; 436/815; 530/395; 530/828; 530/843

[58] Field of Search .............. 435/7, 172.2, 240.26, 435/240.27, 810; 436/501, 512, 548, 808, 813, 815; 530/395, 828, 843

[56] References Cited

U.S. PATENT DOCUMENTS

| | | | |
|---|---|---|---|
| 4,363,799 | 12/1982 | Kung et al. | 424/85 |
| 4,489,167 | 12/1984 | Ochi et al. | 530/828 X |
| 4,579,827 | 4/1986 | Sakamoto et al. | 436/813 X |
| 4,818,682 | 4/1989 | Linnane | 436/813 X |

OTHER PUBLICATIONS

Blaszczyk, M. et al., Cancer Research 44: 245–253 (1984).
DeLellis et al., (1987), Seminars in Oncology 14: 173–192.
Niles et al., (1987), Cancer Investigation 5: 545–552.
Schoentag et al., (1987), Cancer Research 47: 1695–1700.
Vecchi et al., (1987), Proc. Natl. Acad. Sci., U.S.A., 84: 3425–3429.
Abe et al., (1986), Cancer Research 46: 2639–2644.
Bleday et al., (1986), Cancer 57: 433–440.
Itzkowitz et al., (1986), Cancer Reserach 46: 2627–2632.
Rogers et al., (1986), Cancer Immunol. Immunother, 23: 107–112.
Sakamoto et al., (1986), Cancer Reserach 46: 1553–1561.
Yuan et al., (1985), Cancer Reserach 45: 4499–4511.
Nadakavukaren et al., (1984), Differentiation 27: 209–220.
Fredman et al., (1983), The Journal of Biological Chemistry 258: 11206–11210.
Wagener et al., (1983), The Journal of Immunology 130: 2308–2315.
Herlyn et al., (1982), Proc. Natl. Acad, Sci., U.S.A., 79: 4761–4765.
Kurzinger et al., (1982), The Journal of Biological Chemistry 257: 12412–12418.
Goslin et al., (1981), The American Journal of Medicine 71: 246–253.
Hsu et al., (1981), The Journal of Histochemistry and Cytochemistry 29: 1349–1353.
Kupchik et al., (1981), Cancer Research 41: 3306–3310.
Morrison, (1980), Methods in Enzymology 70: 214–220.
Herlyn et al., (1979), Eur. J. Immunol. 9: 657–659.
Springer et al., (1979), Journal of Surgical Oncology 11: 95–106.
Ey et al., (1978), Biochemistry 15: 429–436.
Springer et al., (1977), Clinical Immunology and Immunopathology 7: 426–441.
Search Report (Paper Chase) Relating Generally to the Field of Tumor-Specific Antigens.
Salem et al., (1987), Surgical Forum (Oct.) pp. 408–410.
Salem et al., (1987), Proceedings of AACR, vol. 28—Immunology, Abstract No. 1571.

Primary Examiner—Robert J. Warden
Assistant Examiner—Jack Spiegel
Attorney, Agent, or Firm—Lahive & Cockfield

[57] ABSTRACT

A new marker for colorectal carcinoma has been discovered which is a glycoprotein having a molecular weight of approximately 160,000 daltons. Assay methods which can identify this marker are useful indetecting, diagnosing, and monitoring colorectal carcinoma, and in particular, carcinoma of the undifferentiated variety which heretofor were not readily detectable. For example, an assay which utilizes an antibody reacting to this glycoprotein marker is useful in a screening method for the detection and monitoring of colorectal carcinoma cells. Such an antibody can be included as part of a kit for screening a patient for colorectal carcinoma.

4 Claims, No Drawings

MARKER FOR COLORECTAL CARCINOMA AND METHODS OF DETECTING THE SAME

BACKGROUND OF THE INVENTION

The U.S. Government has rights in this invention pursuant to National Cancer Institute Grant Nos. CA 44583 and CA 44704.

CROSS-REFERENCE TO RELATED APPLICATION

The subject matter of this application is related to that of copending application Ser. No. 183,831, assigned to the assignees of this application, entitled "*Monoclonal Antibody for Colorectal Carcinoma*", filed on even date herewith.

The present invention relates to the field of cancer diagnosis, and more specifically to the identification of new cancer markers and methods useful in the diagnosis, detection, and monitoring of human colorectal carcinoma.

Colorectal carcinoma is a cancer which affects many people per year. The prognosis is poor in about 50% of the cases because the tumor is often not detected until the disease has spread and has reached a terminal stage. Early diagnosis is important to increase chances of arresting the carcinoma before it metastasizes, thereby leading to an improved prognosis.

A widely used method of the identification of cancerous tissue is to determine its structural resemblance to fetal or immature tissue. In this way, tumors can be classified depending on the degree of cellular differentiation; they can be undifferentiated, poorly differentiated, moderately differentiated or well differentiated. In addition, the behavior of a given tumor can often be related to its degree of differentiation. For example, poorly differentiated tumors tend to grow more rapidly and metastasize earlier than do differentiated tumors which more closely resemble the tissue of origin. Poorly differentiated tumors tend to have a poor prognosis and are difficult to detect.

One method of early tumor diagnosis is detection of the presence of a marker or antigen specific for a particular tumor. These normally proteinaceous markers are synthesized by the tumor, and may be found in the serum and/or on the surface of the tumor. Only a limited number of tumor markers for colorectal carcinoma have thus far been found to have clinical use. These include carcinoembryonic antigen (CEA), and the sialyated Lewis a antigen (CA 19.9). Unfortunately, approximately 40% of patients whose condition has been accurately diagnosed as colorectal carcinoma do not have elevated plasma levels of either of these antigens when initially examined. There is no commercially available serodiagnostic marker which can be used to detect the tumor and to monitor therapy for this group.

Production of some tumor markers e.g., CEA and CA 19.9, by tumor cells in vitro correlates with a greater degree of cellular differentiation. For example, CEA and CA 19.9 are present to a far lesser degree on poorly differentiated or undifferentiated cancer cells than on those which are more differentiated. Accordingly, many patients with undifferentiated colorectal carcinomas never develop elevated serum levels of either of these markers, even in the terminal stages of the cancer. There is also considerable overlap between the presence of CA 19.9 and CEA, the patient with a normal CEA level and an elevated level of CA 19.9 being the exception rather than the rule. Therefore, new markers suitable for identifying and monitoring undifferentiated tumors would be of great value.

Accordingly, it is an object of this invention to provide a new marker for the detection of colorectal carcinoma.

It is another object of the invention to provide a new marker suitable for diagnosing and monitoring colorectal carcinoma, and in particular, undifferentiated or poorly differentiated colorectal carcinoma for which known characterizing markers are not present.

A further object of the present invention is to provide a method and kit for the detection and monitoring of colorectal carcinoma in patients using assay methods specific for markers on colorectal carcinoma cells.

A still further object is to provide screening procedures for detecting the presence of colorectal carcinoma cells at all stages of differentiation.

SUMMARY OF THE INVENTION

A new tumor marker for human colorectal carcinoma (hereinafter referred to as the CC glycoprotein) has been discovered with the use of an antibody raised to an undifferentiated tumor cell line. This marker is a glycoprotein of approximately 160,000 daltons molecular weight, and is found on the surface of undifferentiated as well as more differentiated colorectal carcinoma cells.

A method for detecting and monitoring human colorectal carcinoma has been developed. This method includes contacting a biological sample with an antibody or portion thereof which reacts with the CC glycoprotein, an analog, or portion thereof, and observing if the antibody reacts with the sample. The biological sample may be whole blood, serum, ascites fluid, a tissue biopsy, a tumor, a tissue culture, or a histological preparation thereof. The antibody may be raised to undifferentiated tumor cells, to the CC glycoprotein, or to analogs or portions thereof. More specifically, this antibody may be a polyclonal or monoclonal antibody, or analog or portion thereof which does not cross-react with CEA, NCA, CA 19.9, alpha-1-acid glycoprotein, or with the blood group substances A, B, and H. An immunoassay may be utilized to observe the extent of reaction between the receptor and the sample.

A detection method has also been developed which enables the diagnosis and identification of a tumor cell in a biological sample from a patient. In this method the sample is subjected to at least one of a plurality of tests, each of which is specific for a particular tumor marker. The test may be any type of assay, preferably an immunoassay which employs an antibody specific for a tumor marker. The tests may be carried out sequentially until one of them indicates the presence of a particular marker.

Further, a kit for screening a patient for colorectal carcinoma has been developed which contains a plurality of different antibodies specific for tumor markers. These antibodies may include those reacting with one of the following markers: CC glycoprotein; CEA; NCA; CA 19.9; and alpha-1-acid glycoprotein.

The foregoing and other objects of the present invention, the various features thereof, as well as the invention itself may be more fully understood from the following description of the invention.

DESCRIPTION

The present invention relates to a marker and method for detecting human colorectal carcinoma. More particularly, it relates to the use of assay methods which enable the detection of the marker. Detection of the marker is indicative of the presence of colorectal carcinomas, such as those which are undifferentiated, which otherwise would not have been detected with antibodies to other tumor markers.

CC glycoprotein, the newly discovered marker has been found on the surface of many tumor cell lines including those which elicit CEA and some which do not. The following procedure describes its isolation from the undifferentiated, non-CEA-producing cell line MIP 101. However, other undifferentiated cell lines could be employed as the starting material as well.

Radiolabeled, undifferentiated MIP 101 tumor cells are lysed with a detergent-containing buffer. The lysate is then subjected to immunoprecipitation procedures using an antibody which reacts with the CC glycoprotein. Polypeptides in the immunoprecipitates are then separated by electrophoresis on polyacrylamide gels containing sodium dodecyl sulfate (SDS), and identified by autoradiography. The marker has thus been identified as the 160,000 dalton CC glycoprotein.

The antibody useful in detecting the marker may be a polyclonal antibody or portion thereof raised to undifferentiated tumor cells, and shown to react with the CC glycoprotein, analogs, and fragments thereof. However, the antibody is most preferably a monoclonal antibody or fraction thereof. It does not cross-react with other known tumor markers such as CEA, CA 19.9, NCA, and alpha-1-acid glycoprotein, or with any of the blood group substances A, B, or H, as determined by established ELISA procedures.

This antibody can be of any class and subclass, but the ND4 monoclonal immunoglobulin produced by the forementioned hybridoma was determined to be of the IgG2a subclass as by the Ouchterlony double diffusion test. This antibody may also be synthesized by biosynthetic or recombinant means, either in whole or in part, and may be linked to other functional molecules such as toxins, dyes, enzymes, or radioactive markers.

The antibody used to detect the marker is a monoclonal antibody called ND4; however, other antibodies which react with the marker are useful as well. The ND4 antibody was obtained from a hybridoma cell line formed upon the fusion of a mouse myeloma cell with a spleen cell from a mouse which had been previously immunized with undifferentiated or nondifferentiated tumor cells. Preferably, non-CEA and/or non-CA 19.9-producing and undifferentiated colorectal cancer cells such as MIP 101 cells are used as the immunizing agent. However, the immunogen alternatively may be the CC glycoprotein, analogs or portions thereof. The mice whose spleen cells were chosen for fusion are preferably from a genetically defined lineage such as Balb/c. The myeloma cells used in the fusion are from a mammalian, antibody-producing cell line, but most preferably are from a mouse cell line, an example being NS-1. The monoclonal antibody can be obtained from ascites fluid of mice injected with the forementioned hybridoma.

The antibody is specific for tumor cells and many fetal tissues, as determined by fluorescence binding studies performed on formalin-fixed cells, and will recognize tumor cells having different degrees of differentiation including some CEA- and/or CA 19.9-producing cells. However, this antibody is particularly useful in recognizing tumor cells which are undifferentiated or poorly differentiated, and which do not elicit detectable levels of CEA and/or CA 19.9.

Alternatively, the antibody may be a polyclonal immunoglobulin obtained from the serum of an animal previously immunized with the CC glycoprotein.

The present invention further provides a method for detecting tumor cells, which includes contacting a biological sample with a receptor which is capable of reacting with the CC glycoprotein, analogs, and fragments thereof, and observing whether the receptor reacts with the sample.

Examples of biological samples which may be examined by this method include tissue biopsies, tumors, blood, serum, ascites fluid, tissue cultures, and histological preparations thereof. A histological preparation of a biological preparation may include a wet mount, a dry mount, a frozen sample, a paraffin-embedded sample, an acrylic-embedded sample, or a sample adapted in any way for microscopic examination.

A reaction between the antibody and a sample may be detected by an assay including, for example, one which is enzyme-linked and one which is immunological. A preferred assay is an immunoassay such as a radioimmunoassay, Western blot, or a nitrocellulose "dot" blot.

The method of the present invention can be employed for diagnostic and prognostic purposes, for example, to monitor the growth of a tumor or the functional status of normal colorectal cells. More specifically, the method can be employed, for example, to diagnose the in vivo presence of tumor cells which are undifferentiated or poorly differentiated, and which do not produce CEA and/or CA 19.9.

This screening method can also be expanded to include the use of monoclonal antibodies which are specific for other tumor markers, such as CEA and CA 19.9, so as to enable the determination of the level of differentiation which a tumor cell has achieved. The presence of CEA or CA 19.9 has been correlated with higher degrees of differentiation while the presence of the CC glycoprotein has been correlated with both high and low degrees of differentiation. Therefore, a tumor cell which tests positively for the CC glycoprotein, but tests negatively for CA 19.9 and CEA is most likely undifferentiated or poorly differentiated.

The instant invention also relates to a method for screening patients for colorectal carcinoma. It includes subjecting a biological sample (as previously defined) to at least one test selected from a plurality of tests, each of which is specific for a colorectal carcinoma cell marker, and correlating the presence of a specific marker with a degree of differentiation of that cell.

The screening method of the present invention includes tests for tumor markers CEA, CA 19.9, NCA, alpha-1-acid glycoprotein, and the CC glycoprotein, as well as any additional markers which indicate the presence of colorectal carcinoma. The tests performed may be assays, for example, to determine enzyme-linked activity, or may be immunoassays which utilize an antibody specific for a particular marker. They may be performed in a sequential manner until the presence of at least one marker has been proven.

Finally, this invention provides a convenient kit for screening biological samples for colorectal carcinoma. This kit includes antisera or antibodies specific for tumor markers such as the CC glycoprotein, NCA, CA 19.9, CEA, alpha-1-acid glycoprotein, and may also include any other relevant antisera or antibodies. Screening may be performed by any immunoassay procedures such as, for example, radioimmunoassay, Western blot analysis, or nitrocellulose "dot" analysis.

The following examples illustrate the best mode of making and practicing the present invention, but are not meant to limit the scope of the invention, since alternative methods may be used to obtain similar results.

EXAMPLE 1

Hybridoma and Monoclonal Antibody Production

Balb/c mice (The Jackson Laboratory, Bar Harbor, Me.; 6-8 weeks old) were immunized with four injections of MIP 101 cells, a colorectal cancer cell line of undifferentiated morphology (Niles, et al., Cancer Invest., in press (Dec., 1987)). The injections were performed one week apart and $5 \times 10^6$ cells were injected on each occasion. The first three injections were given intraperitoneally, and the fourth intravenously. Cells were injected with complete Freunds adjuvant on the first occasion, incomplete adjuvant on the second and third occasions, and without adjuvant on the last occasion. Serum withdrawn prior to the last injection showed prominent binding to both the immunogen (MIP 101 cells) and another poorly differentiated cell line, Clone A (derived from DLD-1 (ATCC No. CCL221) by D. Dexter, Roger Williams Hosp., Providence, R.I., now at Dupont, Wilmington, Del.) using a solid phase microtiter plate enzyme-linked immunoassay. The mouse with the best immune response was sacrificed three days after the last injection.

Hybridomas were produced by fusion of spleen cells from the sacrificed mouse with NS-1 (P3NS-1/1-Ag4-1) myeloma cells (American Type Culture Collection, Rockville, Md.; Acc. No. TIB18). In the present example, the method of Nadakavukaren (*Differentiation* 27: 209-202, (1984)) was employed to perform the fusions. Resultant clones were tested for binding to MIP 101 cellas and to Clone A. Subcloning by serial dilution was carried out on one clone. The most productive subclone was injected into the peritoneal cavity of Balb/c mice to produce ascites fluid containing monoclonal antibody. The hybridoma which produces this subclone was deposited with the American Type Culture Collection (Rockville, Md.; ATCC No. HB 9600) on 12/8/87. The ascites fluid obtained was centrifuged, tested for activity, and then stored at $-70°$ C. until required. This source all subsequent investigations.

EXAMPLE 2

Characterization of Resulting Monoclonal Antibodies

A. Binding of Monoclonal Antibodies to Cell Lines In Vitro.

Binding studies were performed on formalin-fixed cells using the ND4 antibody and rhodamine conjugated rabbit anti-mouse antiserum. In the present example, the method of Bleday et al. (Cancer 57: 443-440, (1986)) was followed. Cells were viewed to determine binding using a Zeiss epiflourescent microscope. Twenty eight different cell lines were examined: fifteen human colorectal lines, including nine which produced CEA and six which did not (Table 1); seven human, non-colorectal carcinoma lines (Table 2); and six normal, non-human cell lines (Table 2). Ascites fluid from an IgG2a-producing mouse myeloma line UPC-10 (Sigma) was used as a negative control antibody. Binding to cell lines was graded "−," "+" or "++" dependant on degree of fluorescence. Cell lines were obtained from several sources. All CCL lines, MCF-7, CRL 1420, CV-1, and A431 were obtained from the American Type Culture Collection. CX-1 was obtained from S. Bernal (Dana-Faber Cancer Institute, Boston, Mass.); Moser was from M. Brattain (Baylor College of Medicine, Houston, Tex.); and EJ, RT112 and MB49 were from I. Summerhayes (New England Deaconess Hospital, Boston, Mass.). DLD-2 and DLD-1-derived Clones A and D were obtained from D. Dexter (Roger Williams Hospital, Providence, R.I., now at Dupont, Wilmington, Del.).

TABLE 1

| HUMAN COLORECTAL CARCINOMA LINE | CEA PRODUCTION (ng/10⁶ cells/ml) | ND4 IMMUNO-FLUORESCENCE |
|---|---|---|
| CCL 235 | 523 | + |
| CCL 238 | 362 | ++ |
| DLD 2 120 | + | |
| CX1 70 | ++ | |
| CCL 222 | 2.5 | ++ |
| CCL 228 | 0.7 | − |
| CCL 231 | 0.6 | ++ |
| CCL 227 | 0.15 | ++ |
| MOSER (+) | | ++ |
| CCL 220 | 0.0 | ++ |
| CCL 220.1 | 0.0 | ++ |
| CCL 224 | 0.0 | ++ |
| MIP 101 | 0.0 | ++ |
| CLONE A | 0.0 | ++ |
| CLONE D | 0.0 | ++ |

TABLE 2

| CELL LINE | TISSUE SOURCE | ND4 IMMUNO-FLUORESCENCE |
|---|---|---|
| CRL 1420 | Human Pancreatic Cancer | − |
| MCF7 | Human Breast Cancer | ++ |
| EJ | Human Bladder Cancer | − |
| RT 112 | Human Bladder Cancer | − |
| A431 | Human Vulval Cancer | − |
| CCL 105 | Human Adrenal Cancer | + |
| CCL 185 | Human Lung Cancer | − |
| LOX | Human Melanoma | − |
| KAPOSI | Human Sarcoma | − |
| CV-1 | Normal Monkey Kidney | − |
| MB49 | Normal Mouse Bladder | + |
| THE | Normal Hamster Stomach | − |
| F111 | Normal Rat Fibroblast | − |
| A31 | Normal Mouse Fibroblast | − |
| CCL 22 | Normal Bovine Kidney | − |

After formalin fixation, indirect immuofluorescence showed rhodamine-conjugated antibody binding to 14 out of 15 human colorectal carcinoma cell lines, with prominent (++) binding to 12 out of 15 (80%) lines. Prominent binding was also seen on all of the 6 non-CEA-producing colorectal carcinoma cell lines. Two of seven human, non-colorectal carcinoma lines and one of six non-human lines also bound the antibody.

B. Immunohistopathology.

Immunohistopathological studies were performed to determine whether the ND4 antibody binds to a cancerous or normal human tissue and if so, on which cells in the tissue section.

Formalin-fixed, paraffin-embedded tissue sections were deparaffinized with xylene and ethanol, rehydrated, and incubated with phosphate buffered saline (PBS) containing 0.3% $H_2O_2$ to block endogenous peroxidase activity. Sections were washed and blocked with 1% horse serum for 30 minutes and then incubated at 4° C. overnight with ND4 antibody. Subsequent staining was performed according to a standard avidin-biotin-immunoperoxidase technique. In the present example, the method of Hsu et al. ((1981) Cytochem. 29:1349–1353) was followed. Tissue specimens were obtained from the Department of Surgery, Deaconess Hospital, Boston, Mass. or the Department of Pathology, Boston City Hospital, 0554 Boston, Mass.

The following tissues were examined: colon carcinoma, including two well differentiated, nine moderately differentiated, and four poorly differentiated or undifferentiated tumors; normal tissue from thirteen different specimens of normal colonic mucosa obtained from patients with either benign colonic diseases or entirely normal colons, or from the margin of colonic resections from patients who had undergone surgery for colorectal cancer; twenty one different normal non-colonic tissue samples obtained by autopsy; and samples from eleven non-colonic tumors, of which two were gastrointestinal in origin. The results are shown in Table 3.

TABLE 3

BINDING OF ND4 MONOCLONAL ANTIBODY TO COLORECTAL CARCINOMA.

| TISSUE | NO. of SAMPLES | % OF SAMPLES BINDING |
| --- | --- | --- |
| Colorectal carcinomas (including 3 of 4 poorly differentiated tumors) | 15 | 60% |
| Normal colonic epithelium | 13 | 15% |
| Normal non-colonic tissue | 21 | 5% |
| Non-colonic tumors | 11 | 9% |

B. Antibody Typing

ND4 antibody was screened for antibody isotype by the Ouchterlony double diffusion test in agar plates against anti IgM, anti IgG, anti IgG1, anti IgG2a, anti IgG2b and anti IgG3 antibodies (Cappell). Precipitating bands were produced only with anti-IgG2a antibodies.

EXAMPLE 3

CC Glycoprotein Isolation

Antigen characterization was performed by immunoprecipitation of MIP 101 cells which had been radiolabelled by three different procedures. Cells were labelled overnight with [$^{35}$S]-methionine, or with [$^{3}$H]-glucosamine (New England Nuclear) according to the method of Kurzinger et al. (J.B.C. 257: 20,12412–12418, (1982)). Cell surfaces of live MIP 101 cells were labelled with $^{125}$Iodine using the lactoperoxidase procedure of Morrison (Methods Enzymol. 70: 214–220 (1980)). The labelled cells were lyzed in RIPA buffer containing 150 mM sodium chloride, 1% Triton-X-100 (Sigma), 0.1% sodium dodecyl sulfate (SDS; Biorad) and 10 mM Tris-HCl pH 7.2, to which 1 mM phenylmethylsulphonyl fluoride (Sigma) was added. Immunoprecipitations were carried out using Protein A-Sepharose (Sigma) to which a goat-anti-mouse whole serum immunoglobulin (Cappell) was linked. The cell lysate was preincubated at 4° C. with the Protein A complex. Immunoprecipitations with ND4 antibody were carried out as previously described (Hsu et al. Cytochem. 29: 1349–1353) 1981)). Precipitations with UPC-10 (Sigma) or without antibody were used as negative controls. Immunoprecipitates were analyzed by SDS-polyacrylamide gel electrophoresis on 10% gels, followed by autoradiography of the dried gels with Kodak X-OMat film. For the [$^{35}$S]-methionine and [$^{3}$H]-glucosamine-labelled cells, the gels were soaked in EnHance (Dupont) for 45 minutes, and were then washed in distilled water for 30 minutes prior to drying and exposure to X-ray film.

Immunoprecipitation of antigen labelled with $^{125}$Iodine, [$^{35}$S]-methionine and [3H]-glucosamine each showed a band of approximately 160,000 daltons molecular weight on SDS-polyacrylamide gels. This band was absent when either control antibody or no antibody was used.

EXAMPLE 4

Characterization of CC Glycoprotein

A. Effect of Trypsin on ND4 Antibody Binding.

To determine if the marker recognized by the ND4 antibody were a protein, MIP 101 cells which were known to have this marker were pretreated with the serine protease, trypsin, to determine if recognition would be affected. Ninety six well, sterile ELISA microtiter plates were seeded with MIP 101 cells which were grown until confluent. Cells were then fixed with 40% formaldehyde at 24° for 15 minutes, and then rinsed twice in PBS. Two lanes of cells were incubated with 1% trypsin (Gibco) at 37° for two hours and two lanes were incubated with PBS as positive controls. All lanes were examined by light microscopy to ensure that cells had not detached from the microtiter plate. Trypsin-treated and PBS-treated wells were incubated for one hour at 37° C. with ND4 antibody in serial dilutions from 1:100 to 1:100,000. The plates were washed and then incubated with peroxidase-conjugated goat-anti-mouse immunoglobulin (Hyclone). After further washes the plates were developed using orthophenyline diamine as a substrate. The plates were read in a Biorad EIA reader at an absorbance of 492 nm. Optical density was plotted against ND4 antibody dilution for both trypsin-treated and PBS-treated lanes.

Trypsin treatment of formalin-fixed MIP 101 cells resulted in loss of >90% of the binding of ND4 antibody to the cells, as determined by the ELISA, indicating that the antigen recognized by the ND4 antibody is present as a polypeptide residing on the surface of MIP 101 cells.

B. Cross-Reactivity with Other Antigens.

Purified CEA, NCA, and alpha-1-acid glycoprotein as well as blood group antigens obtained from saliva of patients of AB and O blood types were bound to wells of ELISA microtiter plates using 0.1 bicarbonate buffer, pH 9.6. After blocking with 3% bovine serum albumen in Tris-buffered saline for one hour at 37° C., the wells were incubated with ND4 antibody and antibodies to blood group substances A, B, and H as positive controls for the saliva-derived antigens. Subsequent reactions were carried out as described for the ELISA procedure mentioned above No cross-reactivity of the ND4 antibody with CEA, NCA, or alpha-1-acid glycoprotein, or with any of the blood group antigens A, B and H was detected by this test.

EXAMPLE 5

Antigen Detection in Patients with Colorectal Cancer

Ascites fluid from two patients, serum from 37 patients with colorectal cancer and serum from 11 normal subjects were assayed for the presence of the CC glycoprotein antigen using a nitrocellulose "dot" immunoassay. Nine of the patients had early stage disease. Five microtiter "dots" of 1:5 dilutions of ND4 antibody-containing ascites fluid or serum in PBS were placed on a nitrocellulose membrane. After allowing these dots to air dry, the membrane was blocked with 3% bovine serum albumen for one hour at 20° C. The membrane was incubated with a 1:100 dilution of ascites fluid at 4° C. overnight, washed with PBS, and incubated with sheep-anti-mouse IgG that had been preabsorbed with a mixture of polymerized whole serum and human IgG (Cappell) for two hours at 20° C. The reaction was developed with 4-chloro-2-napthol and $H_2O_2$.

Nitrocellulose dot immunoassays of serum from patients with colorectal cancer showed positive reactions in 15 of 37 patients (41%). Three patients had early stage disease and had CEA levels of less than 2.5 ng/ml. Three patients with positive assays prior to resection of their primary tumor had negative reactions postoperatively.

As illustrated by the forementioned examples, a hybridoma-derived monoclonal antibody which reacts with a newly discovered tumor marker, CC glycoprotein has been produced, characterized, and successfully employed to detect colorectal carcinomas which may otherwise would not have been detected with antisera specific for other tumor markers.

The invention may be embodied in other specific forms without departing from the spirit or essential characteristics thereof. The present embodiments are therefore to be considered in all respects as illustrative and not restrictive, the scope of the present invention being indicated by the appended claims rather than by the foregoing description, and all the changes which come within the meaning and range of equivalency of the claims are therefore intended to be embraced therein.

We claim:

1. A method of detecting human colorectal carcinoma comprising the steps of:
   (a) contacting a biological sample with an antibody or portion thereof which reacts with CC glycoprotein, analogs, or fragments thereof, CC glycoprotein having a molecular weight of approximately 160,000 daltons, and not cross-reacting with antibodies to any of carcinoembryonic antigen, CA 19.9, alpha-1-acid glycoprotein, nonspecific crossreacting antigen, or to any of blood group substances A, B, or H; and
   (b) observing whether said antibody reacts with said sample,
   an observation of a reaction with said sample indicating the presence of human colorectal carcinoma.

2. The method of claim 1 wherein said antibody comprises a monoclonal antibody, analog, or fragment thereof capable of reacting with CC glycoprotein.

3. The method of claim 1 wherein said sample comprises biological material selected from a group consisting of tumors, whole blood, serum, ascites fluid, and tissue biopsies, tissue cultures, and in vitro histological preparations thereof.

4. A kit for screening a patient for colorectal carcinoma, said kit comprising antisera specific for at least one marker for colorectal carcinoma, said marker including the CC glycoprotein, and said screening is carried out by subjecting a tissue sample from said patient to immunoassay procedures utilizing said antisera.

* * * * *